United States Patent [19]

Müller

[11] 4,360,525

[45] Nov. 23, 1982

[54] DIBENZAZEPINE DERIVATIVES, PHARMACEUTICAL COMPOSITIONS CONTAINING THEM, AND METHODS OF USE

[75] Inventor: Werner Müller, Gümlingen, Switzerland

[73] Assignee: Sandoz Ltd., Basel, Switzerland

[21] Appl. No.: 306,974

[22] Filed: Sep. 29, 1981

Related U.S. Application Data

[63] Continuation-in-part of Ser. No. 190,669, Sep. 25, 1980, abandoned.

[30] Foreign Application Priority Data

Oct. 1, 1979 [CH] Switzerland .......................... 8836/79
Dec. 20, 1979 [CH] Switzerland ........................ 11322/79
Jan. 14, 1980 [CH] Switzerland ............................ 268/80

[51] Int. Cl.$^3$ .................. A61K 31/445; C07D 401/04; C07D 413/04; C07D 417/04
[52] U.S. Cl. .................................... 424/267; 546/198; 546/199

[58] Field of Search ................. 546/198, 199; 424/267

[56] References Cited

FOREIGN PATENT DOCUMENTS

111215 6/1964 Czechoslovakia .................. 436/198
108354 12/1966 India ................................... 546/198
961105 6/1964 United Kingdom ................. 260/239

OTHER PUBLICATIONS

Buerki et al., "European J. Med. Chim. Ther.", vol. 13, No. 5, pp. 479-485 (1978).
Kovar et al., "Coll. Chem. Czech.", vol. 43, pp. 2064-2081 (1978).

*Primary Examiner*—Robert T. Bond
*Attorney, Agent, or Firm*—Gerald D. Sharkin; Robert S. Honor; Joseph J. Borovian

[57] ABSTRACT

Dibenzazepine derivatives in free base form or in pharmaceutically acceptable acid addition salt form are useful as neuroleptic, antidepressant, sleep-inducing, sleep-promoting and sleep-prolonging agents.

36 Claims, No Drawings

DIBENZAZEPINE DERIVATIVES, PHARMACEUTICAL COMPOSITIONS CONTAINING THEM, AND METHODS OF USE

This is a continuation in part of application Ser. No. 190,669 filed on Sept. 25, 1980, now abandoned.

The present invention relates to dibenzazepine derivatives, their production and pharmaceutical compositions containing them.

The present invention provides 10-(4-piperidinyl)-10,11-dihydro-dibenz[b,f][1,4]oxazepines, -dibenzo[b,f][1,4]thiazepines and -5H-dibenzo[b,e][1,4]diazepines.

These compounds are hereinafter referred to as compounds of the invention. It is to be appreciated that the compounds of the invention may be optionally substituted in any position.

The present invention further provides a compound of formula I,

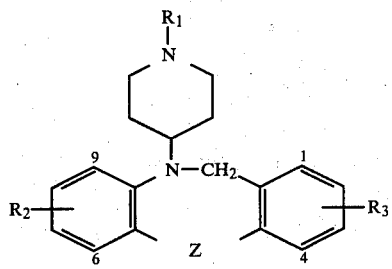

wherein $R_1$ is hydrogen, $C_{1-4}$-alkyl, $C_{2-4}$-alkyl substituted by cyano, $C_{2-5}$-hydroxyalkyl, $C_{2-18}$-alkanoyloxy-$(C_{2-5})$-alkyl, $C_{7-9}$-phenylalkyl, $C_{3-6}$-cycloalkyl or $C_{4-7}$-cycloalkylalkyl, $R_2$ and $R_3$ are independently of each other hydrogen, halogen, trifluoromethyl, $C_{1-4}$-alkyl, $C_{1-4}$-alkoxy or $C_{1-4}$-alkylthio, and Z is —O—, —S— or —NR—, wherein R is hydrogen, $C_{1-4}$-alkyl, $C_{3-5}$-alkenyl, $C_{7-9}$-phenylalkyl, $C_{3-6}$-cycloalkyl or $C_{4-7}$-cycloalkylalkyl.

In formula I, any alkyl, alkoxy or alkylthio radical of 1 to 4 carbon atoms, has preferably 1 to 3 carbon atoms, especially 1 and 2 carbon atoms. The alkyl moiety of cyanoalkyl, hydroxyalkyl, phenylalkyl or cycloalkylalkyl has preferably 2 or 3 carbon atoms. Preferably the hydroxy group in free form or in acylated form or the cyano group is attached to a carbon atom other than the carbon atom adjacent to the nitrogen atom. Substituted alkyl, e.g. cyanoalkyl, hydroxyalkyl, phenylalkyl or cycloalkylalkyl, has the substituent preferably in the terminal distal position. Cycloalkyl or the cycloalkyl moiety of cycloalkylalkyl is conveniently cyclopentyl and especially cyclopropyl. The alkyl moiety of cycloalkylalkyl has conveniently 1 carbon atom. Halogen means fluorine, chlorine, bromine or iodine. Halogen is conveniently fluorine, chlorine or bromine, preferably fluorine or chlorine. The double bond of alkenyl is preferably not in the α,β-position. Alkenyl is conveniently allyl or 2-methylallyl.

$R_1$ is preferably hydrogen or alkyl.
$R_2$ is preferably hydrogen.
$R_3$ is preferably hydrogen or especially halogen.
$R_3$ is conveniently in the 2-position.

Z is preferably —O—, —S— or —N(CH$_3$)—.

It is to be appreciated that when Z is —O— or —S—, a compound of formula I is called a 10-(4-piperidinyl)-10,11-dihydro-dibenz[b,f][1,4]oxazepine or 10-(4-piperidinyl)-10,11-dihydro-dibenzo[b,f][1,4]thiazepine, but when Z is —NR— the compound is more correctly under Chemical Abstracts nomenclature referred to as a 10-(4-piperidinyl)-10,11-dihydro-5H-dibenzo[b,e][1,4]diazepine, rather than a 10-(4-piperidinyl)-10,11-dihydro-5H-dibenzo[b,f][1,4]diazepine.

The present invention in another aspect provides a process for the production of a compound of the present invention which comprises reducing an appropriate 10-(4-piperidinyl)-dibenz[b,f][1,4]oxazepin-11(10H)-one, -dibenzo[b,f][1,4]thiazepin-11(10H)-one and -dibenzo[b,e][1,4]diazepin-11(10H)-one.

The present invention also provides a process for the production of a compound of formula I as defined above which comprises reducing a compound of formula II,

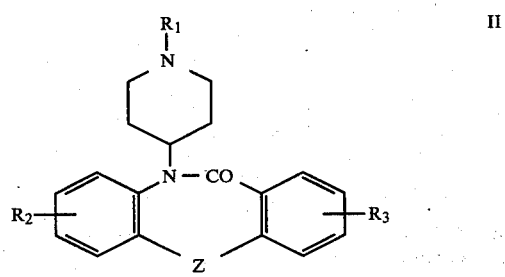

wherein $R_1$, $R_2$, $R_3$ and Z are as defined above.

The reduction may be effected in any conventional manner for the reduction of a lactam.

The reaction may be carried out using appropriate reducing agents, e.g. diborane, lithium aluminium hydride, lithium aluminium hydride/chloroform or sodium acetoxyborohydride. Suitable solvents include tetrahydrofuran or diethylether. Appropriate reaction temperatures may be from room temperature to the reflux temperature of the solution.

Compounds of formula IIa,

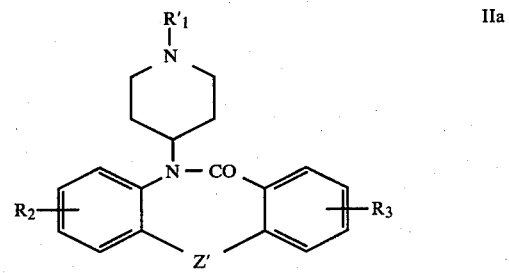

wherein $R_2$ and $R_3$ are as defined above, Z' is —O— or —S— and $R_1'$ has the same significance as $R_1$ except that it is not hydrogen, may, for example, be prepared by cyclising a compound of formula III,

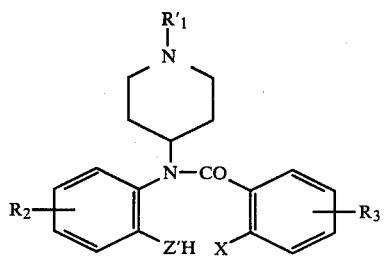

wherein $R_1'$, $R_2$, $R_3$ and $Z'$ are as defined above and X is fluorine, chlorine or bromine.

Compounds of formula III may, for example, be obtained by reacting a compound of formula IV,

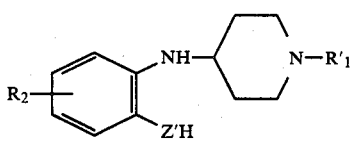

wherein $R_1'$, $R_2$ and $Z'$ are as defined above, with a compound of formula V,

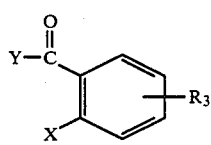

wherein $R_3$ and X are as defined above and Y is a leaving group, e.g. chlorine.

Compounds of formula IV, wherein $Z'$ is —O—, may, for example, be prepared by splitting off the ether group in a compound of formula VI,

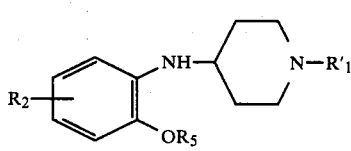

wherein $R_1'$ and $R_2$ are as defined above and $R_5$ is $C_{1-4}$-alkyl or benzyl.

Compounds of formula VI may, for example, be prepared by reacting a compound of formula VII,

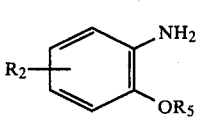

wherein $R_2$ and $R_5$ are as defined above, with a compound of formula VIII,

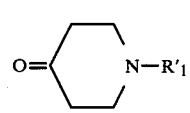

wherein $R_1'$ is as defined above, under reductive conditions.

Compounds of formula IV, wherein $Z'$ is —S—, may, for example, be obtained by reducing a compound of formula IX,

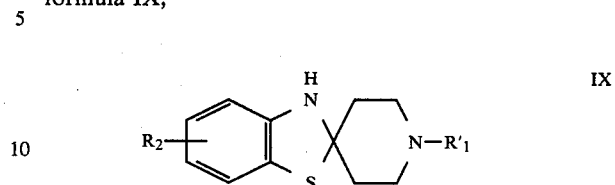

wherein $R_1'$ and $R_2$ are as defined above, in conventional manner, e.g. with lithium aluminium hydride or diborane.

Compounds of formula IX may be prepared by reacting a compound of formula X,

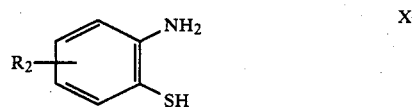

wherein $R_2$ is as defined above, with a compound of formula VIII.

Compounds of formula IIb,

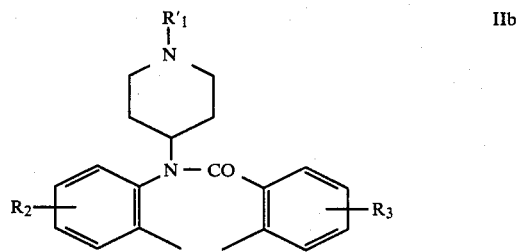

wherein $R_1'$, $R_2$ and $R_3$ are as defined above, may, for example, be prepared by cyclising a compound of formula XI,

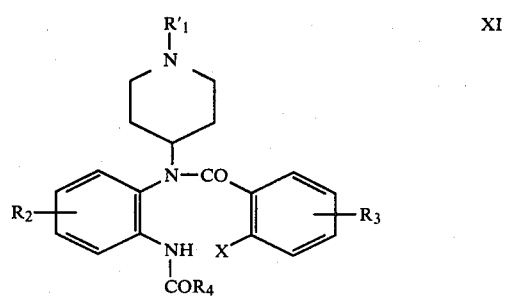

wherein $R_1'$, $R_2$, $R_3$ and X are as defined above, and $R_4$ is hydrogen, trifluoromethyl, $C_{1-4}$-alkyl or $C_{1-4}$-alkoxy.

Compounds of formula XI may, for example, be prepared by reacting a compound of formula XII,

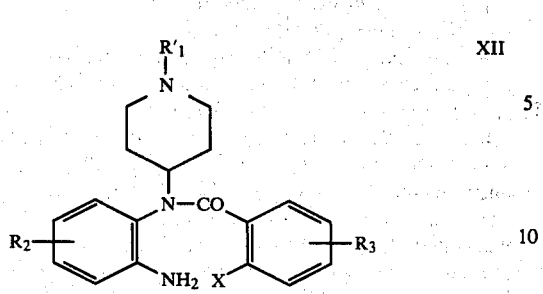

XII wherein $R_1'$, $R_2$, $R_3$ and X are as defined above, with a compound of formula XIII,

R4—CO—Y'  XIII wherein $R_4$ is as defined above and Y' is a leaving group.

Compounds of formula XII may, for example, be obtained by reducing a compound of formula XIV,

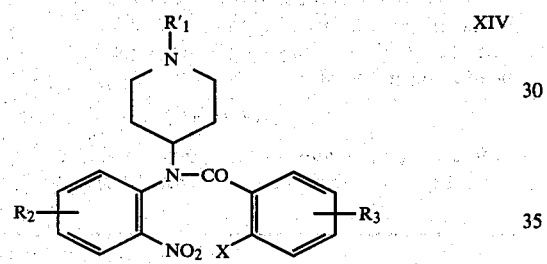

XIV wherein $R_1'$, $R_2$, $R_3$ and X are as defined above.

Compounds of formula XIV may, for example, be prepared by reacting a compound of formula XV,

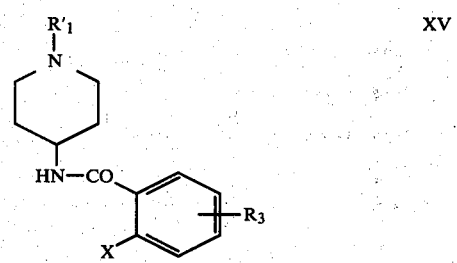

XV wherein $R_1'$, $R_3$ and X are as defined above, with a compound of formula XVI,

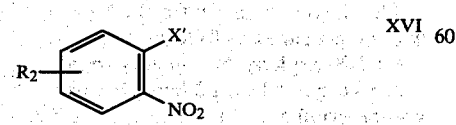

XVI wherein $R_2$ is as defined above and X' is fluorine or chlorine.

Compounds of formula IIc,

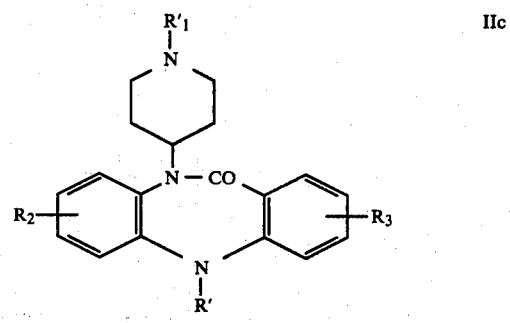

IIc wherein $R_1'$, $R_2$ and $R_3$ are as defined above, and R' has the same significance as R except that it is not hydrogen, may be prepared by reacting a compound of formula IIb with a compound of formula XVII,

R'—Y''  XVII wherein R' is as defined above and Y'' is e.g. halogen, arylsulfonate or alkylsulfonate.

Compounds of formula IId,

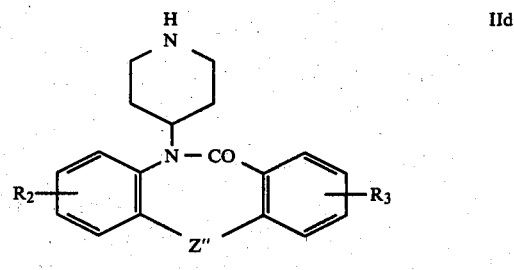

IId wherein $R_2$ and $R_3$ are as defined above, and Z'' is —O—, —S— or —NH— may, for example, be obtained by splitting off a group $R_1''$ in a compound of formula IId',

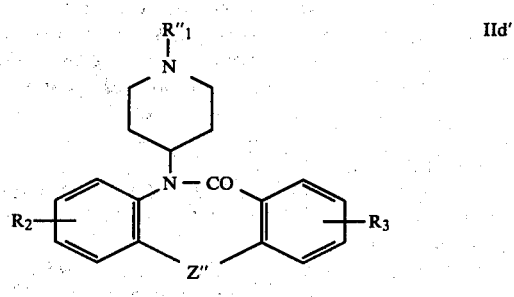

IId' wherein $R_2$, $R_3$ and Z'' are as defined above and $R_1''$ is $C_{1-4}$-alkyl or benzyl.

Compounds of formula IIc',

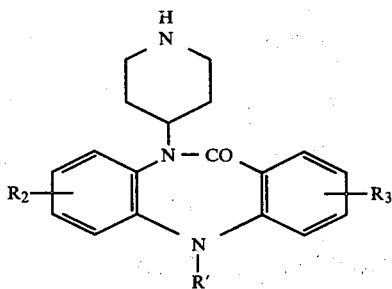

wherein $R_2$, $R_3$ and $R'$ are as defined above, may, for example, be prepared by reacting a compound of formula IId, wherein $Z''$ is —NH— with a chloroformate or bromoformate, e.g. vinyl chloroformate, reacting the resultant N-piperidinyl carbamate with a compound of formula XVII and removing the carbamate group.

Insofar as the production of starting materials is not particularly described these compounds are known or may be produced in analogous manner to known compounds or to processes described herein.

Free base forms of the compounds of the invention may be converted into acid addition salt forms in conventional manner and vice versa. Suitable acids include, for example, hydrochloric acid, hydrobromic acid, maleic acid, fumaric acid and succinic acid.

In the following examples all temperatures are given in degrees Centigrade and are uncorrected.

In the Table the following abbreviations are used:
(1) dihydrobromide
(2) maleate
(3) dihydrochloride
(4) hydrochloride
(5) decomposition
(6) free base

EXAMPLE 1

2-Chloro-10-(1-methyl-piperidin-4-yl)-10,11-dihydro-dibenzo[b,f][1,4]thiazepine

To a suspension of 2.8 g lithium aluminium hydride in 85 ml absolute tetrahydrofuran is added first dropwise at 0° to 5° 1.95 ml of chloroform and thereafter at the same temperature a solution of 8.0 g 2-chloro-10-(1-methyl-piperidin-4-yl)-dibenzo[b,f][1,4]thiazepin-11(10H)-one in 80 ml of absolute tetrahydrofuran. The mixture is stirred at room temperature for 5 hours. To the mixture is then added dropwise under ice cooling 16.8 ml of a saturated solution of potassium carbonate. The precipitate is filtered off and washed with ether. The filtrate is then evaporated and the residue treated with ethanol and hydrobromic acid, to give the dihydrobromide of the heading compound, which upon recrystallisation from ethanol/ether has a m.p. of 257°–260° (decomp.). The succinate of the heading compound has a m.p. of 165°–167°.

The starting material 2-chloro-10-(1-methyl-piperidin-4-yl)-dibenzo[b,f][1,4]thiazepin-11(10H)-one may be obtained as follows:

(a) 1'-methyl-spiro[benzothiazolin-2,4'-piperidine]

A mixture of 125.5 g 2-amino-thiophenol, 147 g N-methyl-4-piperidone, 2 ml acetic acid and 400 ml toluene is refluxed with a water separator for 2 hours. The mixture is evaporated in vacuo. The residue is recrystallised from methylene chloride/ether/petroleum ether to give the heading compound, m.p. 135°–140°.

(b) 2-Chloro-10-(1-methyl-piperidin-4-yl)-dibenzo[b,f][1,4]thiazepin-11(10H)-one A solution of 243 g 1'-methyl-spiro[benzothiazolin-2,4'-piperidine] in 500 ml absolute tetrahydrofuran is added dropwise at 0° to a stirred suspension of 30.4 g lithium aluminium hydride in 1.5 l of tetrahydrofuran. The mixture is stirred 2 hours at 0° and then treated under ice-cooling with 182 ml of a saturated solution of potassium carbonate. The precipitate is filtered off and washed with ether. 543 g of the dried precipitate containing a compound of formula IV, wherein $Z'$=S, $R_1'$=CH$_3$ and $R_2$=H, 235 g 5-chloro-2-fluorobenzoyl chloride, 152 ml triethylamine and 1.6 l benzene are refluxed for 16 hours. The mixture is evaporated in vacuo, the residue treated with 2.2 l of 2 N sodium hydroxide and boiled at reflux for 5 hours. The cooled reaction mixture is extracted with methylene chloride, the organic phase dried and evaporated. The resulting residue containing a compound of formula III, wherein $Z'$=S, $R_1'$=CH$_3$, $R_2$=H, $R_3$=5-Cl and X=F, is dissolved in 350 ml dimethylformamide, treated with 7.0 g of a 55% sodium hydride/oil dispersion and stirred at 80° for 9 hours. The solvent is evaporated in vacuo and the residue partitioned between 2 N hydrochloric acid and toluene. The acid phase is made alkaline with sodium hydroxide and extracted with methylene chloride. After drying the organic phase is evaporated in vacuo and the residue recrystallised from ether to give the heading compound, m.p. 164°–165°.

EXAMPLE 2

In analogous manner to that described in Example 1, the following compounds of formula I are obtained:

| Ex. | $R_1$ | $R_2$ | $R_3$ | Z | m.p. |
|---|---|---|---|---|---|
| a | CH$_3$ | H | H | S | 205–225[(1)(5)] |
| b | CH$_3$ | H | 2-F | S | 207–208[(2)] |
| c | CH$_2$CH$_2$–⟨⟩ | H | 2-Cl | S | 195–200[(1)(5)] |
| d | CH$_2$CH$_2$CN | H | 2-Cl | S | 215–220[(4)(5)] |
| e | H | H | H | S | decomp. from 190[(1)] |
| f | CH$_3$ | H | 2-Br | S | 213–215[(2)] |
| g | H | H | 2-Cl | S | 190–194[(2)] |
| h | CH$_2$CH$_2$OH | H | 2-Cl | S | 153–154[(2)] |
| i | H | H | H | O | 195–196[(2)] |
| j | CH$_2$CH$_2$CN | H | 2-Cl | O | 210–220[(4)(5)] |
| k | CH$_3$ | 8-Cl | H | O | 195–205[(1)(5)] |
| l | CH$_3$ | H | H | O | 150–157[(3)] |
| m | CH$_3$ | H | 2-Br | O | 132–134[(6)] |
| n | CH$_3$ | H | 2-Cl | O | 110–111[(6)] |
| o | CH$_3$ | H | 2-CF$_3$ | O | 167–168[(2)] |
| p | CH$_3$ | H | 2-F | O | 179–180[(2)] |
| q | H | H | 2-F | O | 203–204[(2)] |
| r | CH$_3$ | H | 3-Cl | O | 182–183[(2)] |
| s | CH$_3$ | H | 2-Cl | NH | 205–210[(3)(5)] |
| t | CH$_3$ | H | 2-Cl | NCH$_3$ | 199–210[(2)] |

The starting material for the Example 2(1) compound may be prepared as follows:

(a) 2-Benzyloxy-N-(1-methyl-piperidin-4-yl)aniline

A mixture of 12.0 g 2-benzyloxyaniline, 6.9 g N-methyl-4-piperidine, 2 ml acetic acid and 400 ml toluene is refluxed with a water separator for 2 hours. The mixture is evaporated in vacuo. The residue is dissolved in 150 ml methanol and treated at 20°–25° under stirring portionwise with 3.6 g of sodium borohydride. After the addition is completed stirring is continued for 30 minutes at room temperature and for 2 hours at 65°. The mixture is carefully treated with 100 ml of 2 N hydrochloric acid and heated for 1 hour. The solvent is evaporated, the remaining aqueous solution is first made neutral with sodium hydroxide and then acidified with diluted acetic acid, extracted with ether, made alkaline with sodium hydroxide and extracted with methylene chloride. The methylene chloride phase is evaporated and the residue dissolved in chloroform/methanol/-conc. ammonia (9:1:0.1) and filtered through silica gel to give the heading compound, m.p. 90°–95°.

(b) 2-Hydroxy-N-(1-methyl-piperidin-4-yl)aniline (compound of formula IV, wherein $Z'=O$, $R_1'=CH_3$ and $R_2=H$)

A solution of 9.0 g 2-benzyloxy-N-(1-methyl-piperidin-4-yl)aniline in 100 ml of glacial acetic acid and 0.6 g of 10% of palladium-on-carbon is hydrogenated at room temperature and normal pressure. The catalyst is filtered off and the filtrate evaporated. The residue is partitioned between aqueous sodium hydroxide (pH 9–10) and ether. The ether phase is washed with brine, dried and evaporated to give the heading compound, m.p. 154°–156° (recrystallised from methylene chloride/ether).

(c) 2-Fluoro-N-(2-hydroxyphenyl)-N-(1-methyl-piperidin-4-yl)benzamide (compound of formula III, wherein $Z'=O$, $R_1'=CH_3$, $R_2=H$, $R_3=H$ and $X=F$)

6 g 2-Hydroxy-N-(1-methyl-piperidin-4-yl)aniline, 6.9 g 2-fluoro-benzoyl chloride, 150 ml benzene and 8.9 ml triethylamine are refluxed for 10 hours. 2 N hydrochloric acid and toluene are added, the acid phase is made alkaline and extracted with methylene chloride. The organic phase is evaporated, the residue treated with 250 ml of 2 N sodium hydroxide solution and refluxed for 3 hours. The mixture is made alkaline and extracted with methylene chloride. The organic phase is dried and evaporated to give the heading compound.

(d) 10-(1-Methyl-piperidin-4-yl)-dibenz[b,f][1,4]oxazepin-11(10H)-one

A mixture of 5.3 g 2-fluoro-N-(2-hydroxyphenyl)-N-(1-methyl-piperidin-4-yl)benzamide, 1.1 g of a 55% sodium hydride/oil dispersion and 80 ml dimethylformamide are stirred at 80° for 18 hours. The reaction mixture is worked up as in Example 1(b) to give the heading compound, m.p. 173°–174.5°.

The starting material for the Example 2s compound may be prepared as follows:

(a) 5-chloro-2-fluoro-N-(1-methyl-4-piperidinyl)-benzamide

A mixture of 23.9 g 4-amino-1-methyl-piperidine, 48.5 g 5-chloro-2-fluoro-benzoyl chloride, 44 ml triethylamine and 550 ml benzene is refluxed for 2 hours. Thereafter the solvent is evaporated off in vacuo and the residue is added dropwise under stirring to water. The solution is made alkaline and extracted with toluene. The toluene phase is dried and evaporated. The residue is recrystallised from methylene chloride/ether/petroleum ether to give the heading compound, m.p. 143°–145°.

(b) 5-chloro-2-fluoro-N-(1-methyl-4-piperidinyl)-N-(2-nitrophenyl)-benzamide

A mixture of 31.3 g 5-chloro-2-fluoro-N-(1-methyl-4-piperidinyl)-benzamide, 5.6 g of 55% sodium hydride/oil dispersion and 250 ml dimethylformamide are stirred at 45° for 40 minutes. Thereafter 29.7 g 2-fluoronitrobenzene are added and stirring is continued at 50° for 80 hours. The solvent is evaporated in vacuo and the residue partitioned between 2 N hydrochloric acid and toluene. The acid phase is made alkaline with 2 N sodium hydroxide and extracted with methylene chloride. The organic phase is dried and evaporated in vacuo to give the heading compound, which recrystallised from ether has a m.p. 164°–166°.

(c) 5-chloro-2-fluoro-N-(1-methyl-4-piperidinyl)-N-(2-aminophenyl)-benzamide

A solution of 32.4 g 5-chloro-2-fluoro-N-(1-methyl-4-piperidinyl)-N-(2-nitrophenyl)-benzamide in 700 ml acetic acid ethyl ester and 2 to 3 g Raney nickel is hydrogenated at room temperature and normal pressure. The precipitated product is dissolved in methanol under warming and the catalyst is filtered off. The filtrate is evaporated and the crystalline residue suspended in ether and filtered, to give the heading compound, m.p. 179°–182°.

(d) 5-chloro-2-fluoro-N-(2-trifluoracetylaminophenyl)-N-(1-methyl-4-piperidinyl)-benzamide 100 ml trifluoracetic acid anhydride are added dropwise to a solution of 20.0 g 5-chloro-2-fluoro-N-(1-methyl-4-piperidinyl)-N-(2-aminophenyl)-benzamide in 200 ml of pyridine and the temperature is kept under 12°. Thereafter the mixture is left overnight at room temperature. The mixture is then evaporated in vacuo and the residue partitioned between diluted aqueous sodium carbonate and methylene chloride. The organic phase is dried, treated with charcoal and evaporated. The residue is recrystallised from diethyl ether/petroleum ether to give the heading compound, m.p. 153°–154°.

(e) 2-chloro-5,10-dihydro-10-(1-methyl-4-piperidinyl)-11H-dibenzo[b,e][1,4]diazepin-11-one A mixture of 20.5 g 5-chloro-2-fluoro-N-(2-trifluoracetylaminophenyl)-N-(1-methyl-4-piperidinyl)-benzamide, 2.0 g of a 55% sodium hydride/oil dispersion and 100 ml hexamethyl phosphorotriamide is stirred 140 hours at 150°. The solvent is evaporated in high vacuo and the residue partitioned between diluted acetic acid and methylene chloride. The organic phase is dried and evaporated in vacuo. The residue is dissolved in a mixture of methylene chloride/methanol/-concentrated aqueous ammonia (9:1:0.1) and chromatographed on 300 g silica gel to yield the title compound, m.p. 238°–242° (recrystallised from methylene chloride).

The starting material for the Example 2(t) compound may be obtained by treating 2-chloro-5,10-dihydro-10-(1-methyl-4-piperidinyl)-11H-dibenzo[b,e][1,4]diazepin-11-one at 45° first with sodium hydride in dimethylformamide and then at 0° with methyl iodide to give 2-chloro-5,10-dihydro-5-methyl-10-(1-methyl-4-piperidinyl)-11H-dibenzo[b,e][1,4]diazepin-11-one, m.p. 151°–152°.

EXAMPLE 3

In analogous manner to that described in Example 1, the following compounds of formula I are obtained:

| Ex. | $R_1$ | $R_2$ | $R_3$ | Z |
|---|---|---|---|---|
| a | —$(CH_2)_3OCOC_{17}H_{35}$ | H | 1-$OC_2H_5$ | O |

-continued

| Ex. | R₁ | R₂ | R₃ | Z |
|---|---|---|---|---|
| b |  | 7-SC₂H₅ | H | O |
| c | n-C₃H₇ | H | 4-S—iC₃H₇ | 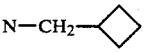 |
| d | H | 6-OC₂H₅ | 3-Br |  |
| e | —CH₂CH₂—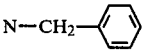 | 8-CF₃ | H | 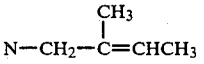 |
| f | H | 9-C₃H₇ | H | $N-CH_2-\underset{\underset{CH_3}{\mid}}{C}=CHCH_3$ |

The compounds of the invention are useful because they possess pharmacological activity in animals and are therefore useful as pharmaceuticals, e.g. for therapy. In particular, the compounds of the invention are useful as neuroleptic agents in the treatment of e.g. psychotic disturbances such as schizophrenia, as indicated in standard tests, e.g. by an inhibition of spontaneous motor activity in mice on p.o. administration of from about 1 to about 50 mg/kg animal body weight of the compounds in accordance with the principles of Caviezel and Baillod (Pharm. Acta Helv. (1958), 33, 465–484). Results obtained are e.g. as follows:

| Compound | ED₅₀ mg/kg p.o. |
|---|---|
| Example 1 | 26 |
| Thioridazine | 26 |

Additionally, the compounds on administration to mice of from about 0.1 to about 10 mg/kg i.p. inhibit the hypermotility induced by 4,α-dimethyl-m-tyramine (H 77/77) in a test carried out according to the principles of J. Buus Lassen, Psychopharmacologia 37, 331–340 (1974). The compounds also increase the sleep phase II in the sleep/wake cycle in the rat carried out according to the principles of H. Kleinlogel et al, European J. Pharmacol. 33, 159–163, 1975, on administration of from 2 to 20 mg p.o. Results obtained are e.g. as follows:

| Compound | Dose | Sleep phase II % of control |
|---|---|---|
| Example 1 | 10 mg/kg p.o. | 131 |
| Clozapine | 10 mg/kg p.o. | 144 |

For the above mentioned use the dosage will, of course, vary depending on the compound employed, mode of administration and therapy desired. However, in general, satisfactory results are obtained with a daily dosage of from about 0.2 mg to about 100 mg per kg animal body weight, conveniently given in divided doses 2 to 4 times a day or in sustained release form. For the larger mammals, the total daily dosage is in the range from about 25 mg to about 600 mg (e.g. from 25 mg to about 100 mg), and dosage forms suitable for oral administration comprise from about 6 mg to about 300 mg (e.g. 6 to 50 mg) of the compounds admixed with a solid or liquid pharmaceutical carrier or diluent. For the Example 1 compound, the indicated daily dosage for larger mammals is from about 300 mg to about 600 mg.

Test data for the other compounds of the invention may be determined routinely. Corresponding daily dosages may be calculated on the basis of their potency relative to the standard substance.

The compounds of the invention are further useful as anti-depressant agents as indicated in standard tests, for example, by an inhibition of tetrabenazine-induced catalepsy and ptosis in rats on intraperitoneal administration of from 5 to 15 mg per kilogram animal body weight of the compound in accordance with the method described by Stille (Arzeimittel-Forsch. 1964, 14, 534).

For the above-mentioned use the dosage will, of course, vary depending on the compound employed, mode of administration and condition to be treated. However, in general satisfactory results are obtained with a daily dosage of from about 0.1 to about 20 mg per kg animal body weight, preferably given in divided doses 2 to 4 times a day, or in sustained release form. For the larger mammals the total daily dosage is in the range from about 5 to about 500 mg and dosage forms suitable for oral administration comprise from about 1.25 to about 250 mg of the compound admixed with a solid or liquid pharmaceutical carrier or diluent.

An example of a daily dosage form is from 5 to 150 mg or from 10 to 500 mg for the larger mammal. Examples of unit dosage forms are from 1.25 to 75 mg or from 2 to 250 mg.

Additionally the compounds of the invention are useful as sleep-inducing, sleep-promoting and sleep-prolonging agents, as indicated in standard tests. For example, in one test according to the principles of H. Kleinlogel, European J. Pharmacol. 33, 159–163 (1975) an increase in the sleep phase II and a decrease of the wake phase is observed after administration to rats of from 0.5 to 80 mg/kg p.o. animal body weight of the compounds.

For the above-mentioned use the dosage will, of course, vary depending on the compound employed, mode of administration and therapy desired. However, in general, satisfactory results are obtained with a daily dosage of from 0.01 mg to about 80 mg per kg animal body weight, conveniently given shortly before retiring to sleep. For the larger mammals, the total daily dosage is in the range from about 1 to about 100 mg.

Examples of daily dosage are from 0.015 to 80 mg/kg or 0.1 to 20 mg. Examples of unit dosage forms for the larger mammals are from 10 to 100 mg.

The compounds of the invention may be administered in pharmaceutically acceptable acid addition salt form. Such acid addition salt forms exhibit the same order of activity as the free base forms. The present invention also provides a pharmaceutical composition comprising a compound of the invention, in free base form or in pharmaceutically acceptable acid addition salt form, in association with a pharmaceutical carrier or diluent. Such compositions may be in the form of, for example, a solution or a tablet.

The neuroleptic activity is the preferred utility. The preferred compound is the Example 1 compound.

In one group of compounds $R_1$ is hydrogen, $C_{1-4}$-alkyl, $C_{2-5}$-hydroxyalkyl, $C_{7-9}$-phenylalkyl, $C_{3-6}$-cycloalkyl or $C_{4-7}$-cycloalkylalkyl, $R_2$ and $R_3$ are independently of each other hydrogen, halogen, trifluoromethyl, $C_{1-4}$-alkyl, $C_{1-4}$-alkoxy, $C_{1-4}$-alkylthio and Z is —O—.

In another group of compounds $R_1$ is hydrogen, $C_{1-4}$-alkyl, $C_{2-5}$-hydroxyalkyl, $C_{7-9}$-phenylalkyl, $C_{3-6}$-cycloalkyl or $C_{4-7}$-cycloalkylalkyl, $R_2$ and $R_3$ are independently of each other hydrogen, halogen, trifluoromethyl, $C_{1-4}$-alkyl, $C_{1-4}$-alkoxy or $C_{1-4}$-alkylthio and Z is —S—.

In another group of compounds $R_1$ is hydrogen, $C_{1-4}$-alkyl, $C_{2-5}$-hydroxyalkyl, $C_{2-4}$-alkyl substituted by cyano, $C_{7-9}$-phenylalkyl, $C_{3-6}$-cycloalkyl or $C_{4-7}$-cycloalkylalkyl, $R_2$ and $R_3$ are independently of each other hydrogen, halogen, trifluoromethyl, $C_{1-4}$-alkyl, $C_{1-4}$-alkoxy or $C_{1-4}$-alkylthio and Z is —NR—, wherein R is hydrogen, $C_{1-4}$-alkyl, $C_{7-9}$-phenylalkyl, $C_{3-6}$-cycloalkyl or $C_{4-7}$-cycloalkylalkyl.

In a subgroup $R_3$ is halogen.

In another group of compounds Z is —O— and $R_2$ and $R_3$ are other than halogen.

In a subgroup of compounds Z is —O— and $R_2$ and $R_3$ are other than chloro.

In a first group of compounds Z is —O—.
In a second group of compounds Z is —S—.
In a third group of compounds Z is —NH—.
In a fourth group of compounds Z is alkylimino.
In a fifth group of compounds Z is alkenylimino.
In a sixth group of compounds Z is phenylalkylimino.
In a seventh group of compounds Z is cycloalkylimino.
In an eighth group of compounds Z is cycloalkylalkylimino.
In a ninth group of compounds $R_1$ is hydrogen.
In a tenth group of compounds $R_1$ is alkyl.
In an eleventh group of compounds $R_1$ is hydroxyalkyl.
In a twelfth group of compounds $R_1$ is phenylalkyl.
In a thirteenth group of compounds $R_1$ is cycloalkyl.
In a fourteenth group of compounds $R_1$ is cycloalkylalkyl.
In a fifteenth group of compounds $R_2$ is hydrogen.
In a sixteenth group of compounds $R_2$ is halogen.
In a seventeenth group of compounds $R_2$ is trifluoromethyl.
In an eighteenth group of compounds $R_2$ is alkyl.
In a nineteenth group of compounds $R_2$ is alkoxy.
In a twentieth group of compounds $R_2$ is alkylthio.
In a twentyfirst group of compounds $R_3$ is hydrogen.
In a twentysecond group of compounds $R_3$ is halogen.
In twentythird group of compounds $R_3$ is trifluoromethyl.
In a twentyfourth group of compounds $R_3$ is alkyl.
In a twentyfifth group of compounds $R_3$ is alkoxy.
In a twentysixth group of compounds $R_3$ is alkylthio.
In a twentyseventh group of compounds $R_1$ is alkyl substituted by cyano.
In a twentyeighth group of compounds $R_1$ is alkanoyloxyalkyl.

I claim:

1. A compound of formula I,

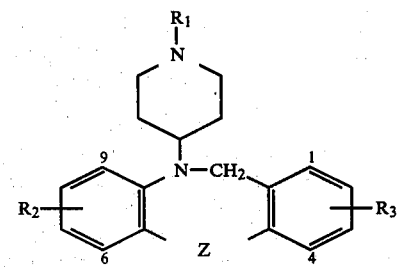

wherein
$R_1$ is hydrogen, $C_{1-4}$-alkyl, $C_{2-4}$-alkyl substituted by cyano, $C_{2-5}$-hydroxyalkyl, $C_{2-18}$-alkanoyloxy-($C_{2-5}$)-alkyl, $C_{7-9}$-phenylalkyl, $C_{3-6}$-cycloalkyl or $C_{4-7}$-cycloalkylalkyl, $R_2$ and $R_3$ are independently of each other hydrogen, halogen, trifluoromethyl, $C_{1-4}$-alkyl, $C_{1-4}$-alkoxy or $C_{1-4}$-alkylthio, and Z is —O—, —S— or —NR—, wherein R is hydrogen, $C_{1-4}$-alkyl, $C_{3-5}$-alkenyl, $C_{7-9}$-phenylalkyl, $C_{3-6}$-cycloalkyl or $C_{4-7}$-cycloalkylalkyl, in free base form or in pharmaceutically acceptable acid addition salt form.

2. A compound of claim 1 wherein $R_1$ is hydrogen, $C_{1-4}$-alkyl, $C_{2-5}$-hydroxyalkyl, $C_{7-9}$-phenylalkyl, $C_{3-6}$-cycloalkyl or $C_{4-7}$-cycloalkylalkyl; $R_2$ and $R_3$ are independently of each other hydrogen, halogen, trifluoromethyl, $C_{1-4}$-alkyl, $C_{1-4}$-alkoxy or $C_{1-4}$-alkylthio; and Z is —O—; in free base form or in pharmaceutically acceptable acid addition salt form.

3. A compound of claim 2 wherein $R_3$ is halogen, in free base form or in pharmaceutically acceptable acid addition salt form.

4. A compound of claim 2 wherein $R_1$ is hydrogen, $C_{1-4}$-alkyl, $C_{2-5}$-hydroxyalkyl, $C_{7-9}$-phenylalkyl, $C_{3-6}$-cycloalkyl or $C_{4-7}$-cycloalkylalkyl; $R_2$ and $R_3$ are independently of each other hydrogen, halogen, trifluoromethyl, $C_{1-4}$-alkyl, $C_{1-4}$-alkoxy or $C_{1-4}$-alkylthio; and Z is —S—, in free base form or in pharmaceutically acceptable acid addition salt form.

5. A compound of claim 4 wherein $R_3$ is halogen, in free base form or in pharmaceutically acceptable acid addition salt form.

6. A compound of claim 2 wherein $R_1$ is hydrogen, $C_{1-4}$-alkyl, $C_{2-5}$-hydroxyalkyl, $C_{2-4}$-alkyl substituted by cyano, $C_{7-9}$-phenylalkyl, $C_{3-6}$-cycloalkyl or $C_{4-7}$-cycloalkylalkyl; $R_2$ and $R_3$ are independently of each other hydrogen, halogen, trifluoromethyl, $C_{1-4}$-alkyl, $C_{1-4}$-alkoxy or $C_{1-4}$-alkylthio; and Z is —NR—, wherein R is hydrogen, $C_{1-4}$-alkyl, $C_{7-9}$-phenylalkyl, $C_{3-6}$-cycloalkyl or $C_{4-7}$-cycloalkylalkyl; in free base form or in pharmaceutically acceptable acid addition salt form.

7. A compound of claim 6 wherein $R_3$ is halogen, in free base form or in pharmaceutically acceptable acid addition salt form.

8. A compound of claim 2 wherein Z is —O— and $R_2$ and $R_3$ are other than halogen, in free base form or in pharmaceutically acceptable acid addition salt form.

9. A compound of claim 2 wherein Z is —O— and $R_2$ and $R_3$ are other than chloro, in free base form or in pharmaceutically acceptable acid addition salt form.

10. A compound of claim 2 which is 2-chloro-10-(1-methyl-piperidin-4-yl)-10,11-dihydro-dibenzo[b,f][1,4]thiazepine, in free base form or in pharmaceutically acceptable acid addition salt form.

11. A compound of claim 2 which is 10-(1-methyl-piperidin-4-yl)-10,11-dihydro-dibenzo[b,f][1,4]thiazepine, in free base form or in pharmaceutically acceptable acid addition salt form.

12. A compound of claim 2 which is 2-fluoro-10-(1-methyl-piperidin-4-yl)-10,11-dihydro-dibenzo[b,f][1,4]thiazepine, in free base form or in pharmaceutically acceptable acid addition salt form.

13. A compound of claim 2 which is 2-chloro-10-[1-(2-phenylethyl)-piperidin-4-yl]-10,11-dihydro-dibenzo[b,f][1,4]thiazepine, in free base form or in pharmaceutically acceptable acid addition salt form.

14. A compound of claim 2 which is 2-chloro-10-[1-(2-cyanoethyl)-piperidin-4-yl]-10,11-dihydro-dibenzo[b,f][1,4]thiazepine, in free base form or in pharmaceutically acceptable acid addition salt form.

15. A compound of claim 2 which is 10-(piperidin-4-yl)-10,11-dihydro-dibenzo[b,f][1,4]thiazepine, in free base form or in pharmaceutically acceptable acid addition salt form.

16. A compound of claim 2 which is 2-bromo-10-(1-methyl-piperidin-4-yl)-10,11-dihydro-dibenzo[b,f][1,4]thiazepine, in free base form or in pharmaceutically acceptable acid addition salt form.

17. A compound of claim 2 which is 2-chloro-10-(piperidin-4-yl)-10,11-dihydro-dibenzo[b,f][1,4]thiazepine, in free base form or in pharmaceutically acceptable acid addition salt form.

18. A compound of claim 2 which is 2-chloro-10-[1-(2-hydroxyethyl)-piperidin-4-yl]-10,11-dihydro-dibenzo[b,f][1,4]thiazepine, in free base form or in pharmaceutically acceptable acid addition salt form.

19. A compound of claim 2 which is 10-(piperidin-4-yl)-10,11-dihydro-dibenz[b,f][1,4]oxazepine, in free base form or in pharmaceutically acceptable acid addition salt form.

20. A compound of claim 2 which is 2-chloro-10-[1-(2-cyanoethyl)-piperidin-4-yl]-10,11-dihydro-dibenz[b,f][1,4]-oxazepine, in free base form or in pharmaceutically acceptable acid addition salt form.

21. A compound of claim 2 which is 8-chloro-10-(1-methyl-piperidin-4-yl)-10,11-dihydro-dibenz[b,f][1,4]oxazepine, in free base form or in pharmaceutically acceptable acid addition salt form.

22. A compound of claim 2 which is 10-(1-methyl-piperidin-4-yl)-10,11-dihydro-dibenz[b,f][1,4]oxazepine, in free base form or in pharmaceutically acceptable acid addition salt form.

23. A compound of claim 2 which is 2-bromo-10-(1-methyl-piperidin-4-yl)-10,11-dihydro-dibenz[b,f][1,4]oxazepine in free base form or in pharmaceutically acceptable acid addition salt form.

24. A compound of claim 2 which is 2-chloro-10-(1-methyl-piperidin-4-yl)-10,11-dihydro-dibenz[b,f][1,4]oxazepine, in free base form or in pharmaceutically acceptable acid addition salt form.

25. A compound of claim 2 which is 2-trifluoromethyl-10-(1-methyl-piperidin-4-yl)-10,11-dihydro-dibenz[b,f][1,4]oxazepine, in free base form or in pharmaceutically acceptable acid addition salt form.

26. A compound of claim 2 which is 2-fluoro-10-(1-methyl-piperidin-4-yl)-10,11-dihydro-dibenz[b,f][1,4]oxazepine, in free base form or in pharmaceutically acceptable acid addition salt form.

27. A compound of claim 2 which is 2-fluoro-10-(piperidin-4-yl)-10,11-dihydro-dibenz[b,f][1,4]oxazepine, in free base form or in pharmaceutically acceptable acid addition salt form.

28. A compound of claim 2 which is 3-chloro-10-(1-methyl-piperidin-4-yl)-10,11-dihydro-dibenz[b,f][1,4]oxazepine, in free base form or in pharmaceutically acceptable acid addition salt form.

29. A compound of claim 2 which is 2-chloro-10-(1-methyl-piperidin-4-yl)-10,11-dihydro-5H-dibenzo[b,e][1,4]diazepine, in free base form or in pharmaceutically acceptable acid addition salt form.

30. A compound of claim 2 which is 2-chloro-5-methyl-10-(1-methyl-piperidin-4-yl)-10,11-dihydro-5H-dibenzo[b,e][1,4]diazepine, in free base form or in pharmaceutically acceptable acid addition salt form.

31. A compound of claim 2 wherein Z is —S—, in free base form or in pharmaceutically acceptable acid addition salt form.

32. A pharmaceutical composition useful in inducing, promoting or prolonging sleep or in treating psychotic disturbances or depressions comprising a pharmaceutically acceptable carrier or diluent and a therapeutically effective amount of a compound of claim 2, in free base form or in pharmaceutically acceptable acid addition salt form.

33. A method of inducing, promoting or prolonging sleep which comprises administering to an animal in need of such treatment a therapeutically effective amount of a compound of claim 2, in free base form or in pharmaceutically acceptable acid addition salt form.

34. A method of treating psychotic disturbances which comprises administering to an animal in need of such treatment a therapeutically effective amount of a compound of claim 2, in free base form or in pharmaceutically acceptable acid addition salt form.

35. A method of treating depressions which comprises administering to an animal in need of such treatment a therapeutically effective amount of a compound of claim 2, in free base form or in pharmaceutically acceptable acid addition salt form.

36. A method of treating psychotic disturbances according to claim 34 which comprises administering to an animal in need of such treatment a therapeutically effective amount of 2-chloro-10-(1-methyl-piperidin-4-yl)-10,11-dihydro-dibenzo[b,f][1,4]thiazepine, in free base form or in pharmaceutically acceptable acid addition salt form.

* * * * *

UNITED STATES PATENT AND TRADEMARK OFFICE
CERTIFICATE OF CORRECTION

PATENT NO. : 4,360,525

DATED : November 23, 1982

INVENTOR(S) : Werner Müller

It is certified that error appears in the above—identified patent and that said Letters Patent is hereby corrected as shown below:

Column 8, in the Table beneath line 33; in Example "t", under the column heading "m.p.", change "199-210$^{(2)}$" to -- 199-201$^{(2)}$ --.

Column 14, directly beneath line 11; delete the structural formula and substitute therefor

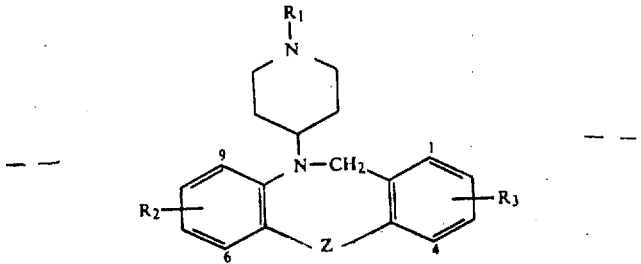

Column 14, line 49; before "wherein", change "2" to -- 1 --.

Column 14, line 60; before "wherein", change "2" to -- 1 --.

Column 15, lines 4 and 7; before "wherein", change "2" to -- 1 --.

UNITED STATES PATENT AND TRADEMARK OFFICE
CERTIFICATE OF CORRECTION

PATENT NO. : 4,360,525

DATED : November 23, 1982

INVENTOR(S) : Werner Müller

It is certified that error appears in the above—identified patent and that said Letters Patent is hereby corrected as shown below:

Column 15, lines 10, 14, 18, 22, 26, 30, 34, 38, 42, 46, 50, 54, 58 and 62; before "which", change "2" to -- 1 --.

Column 16, lines 3, 7, 11, 15, 19, 23 and 27; before "which", change "2" to -- 1 --.

Column 16, line 31; before "wherein", change "2" to -- 1 --.

Column 16, lines 38, 44, 49 and 54; after "claim", change "2" to -- 1 --.

Signed and Sealed this

Nineteenth Day of April 1983

[SEAL]

Attest:

GERALD J. MOSSINGHOFF

Attesting Officer    Commissioner of Patents and Trademarks